United States Patent [19]

Ono

[11] Patent Number: 5,304,976
[45] Date of Patent: Apr. 19, 1994

[54] CONTACT COMBUSTION TYPE CARBON MONOXIDE SENSOR

[75] Inventor: Yoshio Ono, 2-23-7, Oaza Tanaka, Matsubuse-cho, Kitakatsushika-gun, Saitama Prefecture, Japan

[73] Assignees: Mori Seisakusho Co., Ltd.; Masami Numata, both of Chiba; Yoshio Ono, Saitama, all of Japan

[21] Appl. No.: 115,845

[22] Filed: Sep. 2, 1993

[30] Foreign Application Priority Data

Sep. 14, 1992 [JP] Japan .................................. 4-271213

[51] Int. Cl.$^5$ .................... H01C 7/00; G01N 31/12
[52] U.S. Cl. .................................. 338/34; 422/94
[58] Field of Search .................... 338/34, 35; 422/83, 422/94, 97

[56] References Cited

U.S. PATENT DOCUMENTS 4,296,399 10/1981 John .................................... 338/34
4,396,899 8/1983 Ohno ................................... 338/34

Primary Examiner—Marvin M. Lateef
Attorney, Agent, or Firm—Koda and Androlia

[57] ABSTRACT

A contact combustion type carbon monoxide sensor having no sensitivity to $H_2$, $C_2H_5OH$ and other gases but having a CO sensitivity of 25 to 50 mV at a bridge voltage of 6 to 12 V and a concentration of 500 ppm. Each coil is made of a Fe.Pd system alloy wire material having a large diameter, a specific resistance value, a Vickers' hardness value and a temperature coefficient values each falling within a specific range. A catalyst comprising $Cu_2O$, $ZnO$, $MnO_2$ and Pt black is formed on the upper surface of the coil of an active portion, and a catalyst comprising CuO and $Cr_2O_3$ is formed on the upper surface of the coil of a dummy portion.

4 Claims, 3 Drawing Sheets

F I G. 1
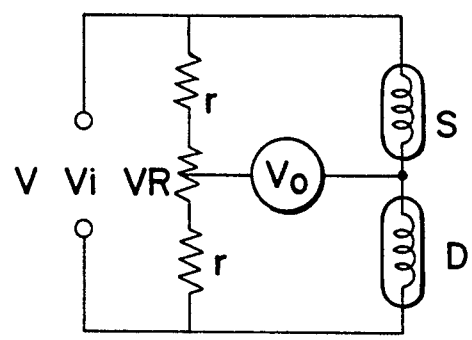
F I G. 2
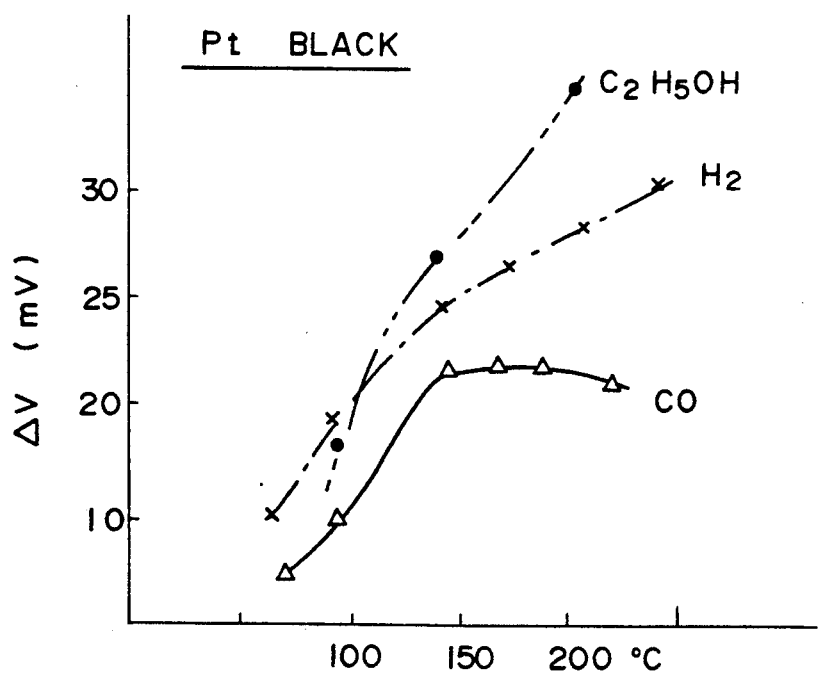

CONTACT COMBUSTION TYPE CARBON MONOXIDE SENSOR

BACKGROUND OF THE INVENTION

1. Field of the Invention

This invention relates to a contact combustion type carbon monoxide sensor which can detect carbon monoxide (hereinafter referred to as "CO") with a high sensitivity at a bridge voltage of 6 to 12 V but hardly has any sensitivity to gases other than CO.

2. Description of the Related Art

CO gas has no color, no taste and no odor and is somewhat lighter in weight than air. When a man breathes for 2 to 3 hours at a CO concentration of 200 ppm, he will surfer from a headache. CO gas has such a high toxicity that when a man breathes for 2 hours at a CO concentration of 1,600 ppm, he will be dead and at a concentration of 3,200 ppm, he will be dead within 10 to 15 minutes.

Standards or required characteristics for CO gas sensors in various countries are generally such that the sensors beep an alarm at a CO concentration of 200 ppm, do not beep any alarm at a $H_2$ concentration of 500 ppm and a $C_2H_5OH$ concentration of 1,000 ppm, and do not have any sensitivity to the other gases. Furthermore, CO gas sensors must not involve an erroneous operation due to the change of a moisture or a temperature or due to the change of a power source voltage, must have high reproducibility and must be free from the change with the passage of time.

BRIEF DESCRIPTION OF THE DRAWINGS

FIG. 1 is a circuit diagram of a contact combustion type CO sensor according to the present invention;

FIG. 2 is a graph showing the sensitivity of the CO sensor to each gas when a Pt black is used as a catalyst;

DESCRIPTION OF THE PREFERRED EMBODIMENTS

Figure 3:
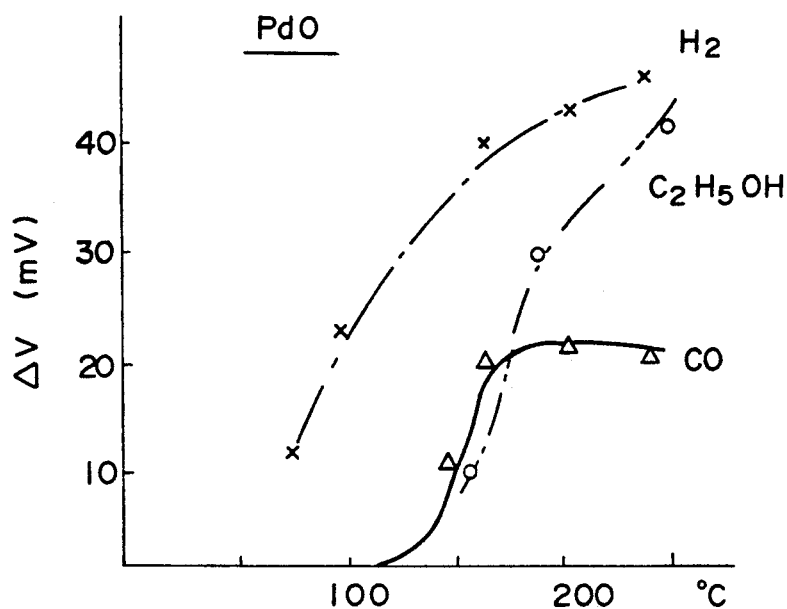
FIG. 3 is a graph showing the sensitivity of the CO sensor to each gas when PdO is used as the catalyst.

The present invention provides a CO gas sensor which has a sensitivity of at least 20 mV at a CO concentration of 500 ppm whereby its sensitivity is limited to 0 to 3 mV at a H, concentration of 500 ppm and to 0 to 3 mV at a $C_2H_5OH$ concentration of 1,000 ppm.

Among the CO sensors, a contact combustion type CO sensor can be used most reliably for a meter application because it has high reproducibility and high gas selectivity. However, conventional contact combustion type CO sensors that have been commercially available are not free from the problem that their gas sensitivity is extremely low.

Generally, the gas sensitivity $\Delta V$ of the contact combustion type gas sensors can be expressed by the following formula:

$$\Delta V = \frac{\Delta R}{4R} \cdot Vi, \quad \Delta R = \alpha \cdot a \cdot m \cdot Q/C \tag{1}$$

Here, $\Delta V$ is the gas sensitivity (output: mV), $\Delta R$ is a coil resistance change value of the coil due to combustion of the gas, R is a coil resistance value of the sensor, Vi is a voltage of a bridge power source V, a is a constant, $\alpha$ is a temperature coefficient of a coil wire material, m is a gas concentration, Q is a molecular combustion heat of the gas, and C is a heat capacity of the sensor.

The contact combustion type CO sensor according to the present invention is constituted as shown in FIG. 1. The sensor is separated into an active portion S and a dummy portion D, each finished in a coil, and these portions S and D are fitted to stems, respectively. A fixed resistor r and a variable resistor VR are disposed, and a bridge power source Vi of D.C. 6 to 12 V is combined. A sensitivity meter Vo is interposed between the midpoint of junction of the active portion S and the dummy portion and the variable resistor VR. In this CO sensor, the sensitivity counter of the sensitivity meter Vo is set to zero when no CO exists.

The present invention aims at providing a CO gas sensor the gas sensitivity of which is as great as possible. It can be understood from the formula (1) given above that in order to increase the gas sensitivity $\Delta V$, it is necessary to increase the voltage Vi of the bridge power source, to increase the temperature coefficient $\alpha$ of the wire material or to reduce the heat capacity C of the sensor.

In the present invention, the voltage of the bridge power source can be increased from 6 V to 9 V and further to 12 V. This object can be accomplished by selectively using a Fe.Pd system alloy wire material having a composition of 15 to 60 wt % of Fe and 40 to 85 wt % of Pd, which has a specific resistance $\rho_{20}$ of 35 to 46 $\mu\Omega$cm, a Vickers' hardness Hv of 200 to 300 and a temperature coefficient T.C.R (0° to 100° C.) of 7,000 to 8,500 ppm/°C., which moreover increase a catalyst surface area and facilitates coil production, and which has a thickness within the range of 15 to 40 $\mu$m.

This wire material can set the sensor temperature to 155°±3° C., and can characterizingly prevent specific oscillation (which vigorously occurs at 177° to 247° C.) that occurs ordinarily when a catalyst such as Pt, Pd, Rh, etc, is used.

In comparison with the conventional Pt wire materials, this wire material can set a specific resistance to a greater value, has a higher temperature coefficient and moreover, has a higher hardness. Accordingly, there can be obtained another advantage that the coil can be produced by far more easily.

In this way, the bridge voltage Vi rises, the sensor sensitivity becomes higher, the production of the coil becomes easier and moreover, a coil having a uniform pitch gap can be produced.

However, the Fe.Pd system alloy wire material has the drawbacks in that its heat resistance and chemical resistance are relatively low. When a catalyst is salified on the surface of the coil, it is almost impossible to apply power to the coil so as to heat the catalyst. Accordingly, a different method must be employed as described later.

The catalyst required for the active portion of the sensor according to the present invention must satisfy the following requirements:

(i) The catalyst has high purity and a high surface concentration, is fine-grained and its activity is also high.
(ii) The catalyst has high activity at a low temperature, and can be machined without corroding the wire material.
(iii) The catalyst has a removing function of H, and $C_2H_5OH$ even at a low temperature.
(iv) The catalyst is an oxide of fine particles which are dispersed uniformly.

As a result of studies, it has been found out that a Pt black has the highest sensitivity to CO followed by PdO among the oxide catalysts.

The Pt black prepared by using $H_2PtCl_6 \cdot 6H_2O$ under the state of an aqueous solution and decomposing it at a low temperature has the highest dispersibility, and has a sufficient CO sensitivity even at a sensor temperature of not higher than 150° C. as shown in FIG. 2.

On the other hand, when PdO is prepared from $PdCl_2$ as the starting material, it does not become complete PdO if a temperature is not higher than 500° C., and since acidicity of a $PdCl_2$ aqueous solution is high, the wire material described above is corroded. Further, PdO does not provide a sufficient CO sensitivity unless the sensor temperature is 170° to 200° C. as shown in FIG. 3.

When the factors described above are taken into consideration, the Pt-black is used as the main catalyst of the active portion. Even with the Pt-black, however, the sensitivity to $H_2$, $C_2H_5OH$, etc, is considerably high, and is about twice the CO sensitivity as shown in FIG. 2. Accordingly, this sensitivity must be eliminated.

A catalyst for effectively removing the $H_2$ sensitivity of the Pt-black is $Cu_2O$ and a catalyst for effectively removing its $C_2H_5OH$ sensitivity is $Cu_2O$-ZnO.

Though $Cu_2O$ has a sensitivity to CO, it does not have sensitivity to $H_2$. However, this compound is not stable and is likely to be oxidized or reduced as represented by the following formula:

$$CuO \rightleftarrows Cu_2O \rightleftarrows Cu$$

Accordingly, it is necessary to fix and stabilize $Cu_2O$ in the form of $Cu_2O$ itself.

Though $Cu_2O$-ZnO has a sensitivity to CO, it does not have a sensitivity to $C_2H_5OH$. Moreover, $Cu_2O$ is easily soluble into ZnO, preferably forms a solid solution and gets stabilized in that form. Nonetheless, the $Cu_2O$-ZnO solid solution does not become active unless the temperature is higher than 170° C. Accordingly, about 10% of $MnO_2$ is added so as to sufficiently activate this solid solution even at a temperature of around 150° C. $Sm_2O_3$ can be used in place of $MnO_2$.

Taken altogether, the present invention uses, as the catalyst for its active portion, a mixture obtained by adding 25 to 35 parts by weight of the Pt-black to 100 parts by weight of a composition comprising 30 to 35 wt % of $Cu_2O$, 50 to 55 wt % of ZnO and 10 to 15 wt % of $MnO_2$.

This catalyst is shaped in a cylindrical form on the coil by first mixing predetermined amounts of aqueous solutions of $Cu(NO_3)_2 \cdot 3H_2O$, $Zn(NO_3)_2 \cdot 6H_2O$ and $Mn(NO_3)_2 \cdot 6H_2O$ to render the mixed solution $NH_4OH$-like, effecting then firing and decomposition to obtain each component oxide in the form of ultra-small particles, and electro-depositing the particles to the coil using a water-soluble resin. Next, the Pt-black is applied in the form of an aqueous solution to the cylindrical surface and thermally decomposed to obtain the catalyst having the composition described above. The properties of the Pt-black such as a specific gravity, an isoelectric point, etc, are remarkably different from those of other oxides. Therefore, if all of them are simultaneously electro-deposited, non-uniformity occurs in a concentration and deposition. For this reason, the Pt-black is added later and thermally decomposed.

Figure 4:
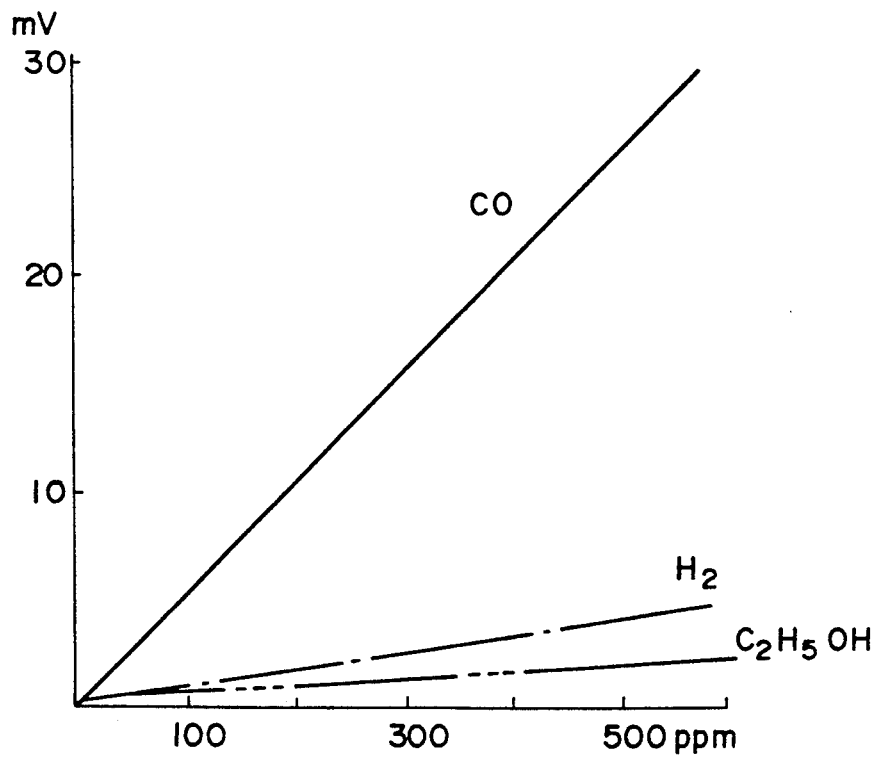
FIG. 4 is a graph showing the sensitivity of the CO sensor to each gas in the present invention.

When the catalyst having the composition described above is used, there can be obtained eventually a sensor having a sensitivity of 20 to 25 mV at CO 500 ppm, 0 to 3 mV at $H_2$ 500 ppm and 0 to 3 mV at $C_2H_5OH$ 1,000 ppm, as typified by an example shown in FIG. 4.

On the other hand, the catalyst applied to the coil of the dummy portion D is selected from those which do not have a CO sensitivity. Moreover, since the dummy portion should compensate for the changes of temperature and humidity, it must satisfy the requirements that the conditions except for the CO sensitivity are common to both of the active portion and the dummy portion, particularly the divided voltage $V_D$ of the dummy portion is equal to that $V_S$ of the active portion, and no zero drift occurs even when any change occurs in the ambient temperature and in the power source voltage.

Figure 5:
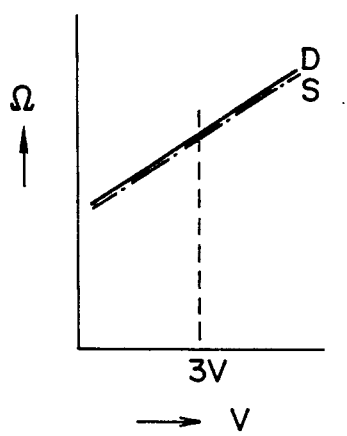
FIG. 5 is a graph showing voltage-resistance characteristics of an active portion and a dummy portion.
Figure 6:
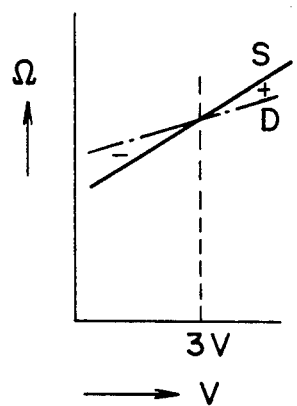
FIG. 6 is a graph showing an example of voltage-resistance characteristics of the active portion and the dummy portion.
Figure 7:
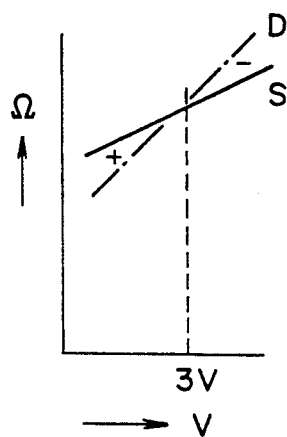
FIG. 7 is a graph showing another example of voltage-resistance characteristics of the active portion and the dummy portion.

FIGS. 5 to 7 are graphs each showing voltage-v-resistance characteristics of the active portion and the dummy portion. As shown first in FIG. 5, when the characteristics of the active portion are substantially parallel to the characteristics of the dummy portion, the zero drift based on the voltage does not occur. In the case of FIG. 6, however, when the voltage rises, the sensitivity becomes positive and in the case of FIG. 7, when the voltage drops, the sensitivity becomes positive. In other words, the sensitivity disadvantageously appears even when the CO gas does not exist. Accordingly, to approximate a heat radiation coefficient of the dummy portion to that of the active portion, a mixture of CuO and $Cr_2O_3$ is applied to the coil of the dummy portion. Further, since the sensor temperature varies with porosity due to catalyst particle size and with adhesion with the wire material, $Al_2O_3$ or TiO is added so as to approximate these conditions to those of the active portion.

In view of the requirements described above, the catalyst of the dummy portion according to the present invention is formed by adding a mixture of 1 part by weight of CuO, 2 parts by weight of $Cr_2O_3$ and 1 part by weight of $Al_2O_3$, to 30 to 40 cc of a resin solution for electrodeposition, pulverizing and thereafter electrodepositing the resultant product.

This catalyst has resistance characteristics almost equal and parallel to those of the active portion in the range of the bridge power source voltage of 6 to 12 V, and the divided voltage $V_S$ of the active portion is kept equal to that of the dummy portion. The zero drift due to the changes in the ambient temperature and in the power source voltage hardly occur and eventually, a desired effect can be obtained by preventing the change of the gas sensitivity.

To sum up, the present invention provides a contact combustion type carbon monoxide sensor, wherein the coils of both of the active portion and the dummy portion are made of the Fe.Pd system alloy wire material having a thickness of 15 to 40 μm, a specific resistance $p_{20}$ of 35 to 45 μΩcm, a Vickers' hardness Hv of 200 to 300 and a temperature coefficient T.C.R (0° to 100° C.) of 7,000 to 8,500 ppm/°C., the catalyst formed at the active portion comprises $Cu_2O$, ZnO, $MnO_2$, and the Pt black, and the catalyst formed at the dummy portion comprises CuO and $Cr_2O_3$.

Embodiment

The coil used for each of the active portion and the dummy portion of the sensor according to the present invention uses a Fe.Pd system alloy wire material having a specific resistance $\rho_{20}°$ C. of 35 to 46 $\mu\Omega$cm, a Vickers' hardness Hv of 200 to 300 and a temperature coefficient T.C.R (0° to 100° C.) of 7,000 to 8,500 ppm/°C., and a trace amount of CO and Mn are added in order to facilitate and stabilize a wire drawing work. The wire material having a thickness within the range of 15 to 40 $\mu$m is selected.

This wire material had a temperature coefficient T.C.R (0° to 100° C.) of at least 7,000 ppm/°C. Accordingly, a sensor having a CO sensitivity several times higher than that of the conventional platinum wire having a temperature coefficient of about 3,800 ppm/°C. can be obtained. Since a specific resistance $\rho_{20}$ of 35 to 46 $\mu\Omega$cm can be secured, the specific resistance is considerably higher than that of the platinum wire, i.e. about 10.6 $\mu\Omega$cm. Accordingly, even when the number of coil windings is reduced, substantially the same resistance value can be retained, and the work efficiency of the winding operation can be drastically improved.

To improve stability, annealing is carried out at a high temperature for a short time in a mixed gas atmosphere of Ar and CO for the alloy wire material according to the present invention. The coil has a winding diameter of 0.8 to 1.0 $\phi$ and the number of turns of 22 to 24, and is fitted horizontally to a stem so that the coil length is 2.5 to 2.8 mm.

The mean temperature of the sensor can be known in advance from the resistance $R_t/R_{20}$ of the coil at 20° C. and/or from the resistance $R_{3v}/R_{20}$ at the time of application of a 3 V voltage. Accordingly, the sensor temperature is determined from the resistance at 20° C. and/or from the resistance at 20° C. at the time of application of a 3 V D.C. When the winding work is completed, the coils having a substantially equal sensor temperature are selected as a pair. When the pair of coils are used for the active portion and the dummy portion, $V_o$ remains almost constant and no zero drift occurred even when any change occurred in the ambient temperature or in the power source voltage.

In the present invention, the sensor temperature was set to 155°±3° C., so as to avoid specific oscillation by CO of the Pt catalyst applied to the active portion at temperatures in the range of 177° to 247° C. When the sensor temperature was set in advance to 155°±3° C., the temperature did not rise beyond 177° C. even when the temperature rise resulting from the combustion of CO at a CO concentration of 1,000 ppm, the rise of the ambient temperature, the rise of the power source voltage, and so forth, were taken into consideration. Accordingly, the oscillation described above did not occur.

Next, a contact combustion type carbon monoxide sensor according to an embodiment of the present invention will be explained. This sensor has the construction shown in FIG. 1.

The sensor uses a 30 $\mu$m-thick Fe.Pd system wire material which is annealed at a high temperature for a short time in the atmosphere of a mixed gas of argon and CO, and has a specific resistance ($\rho_{20}$) of 40 $\mu\Omega$cm, a Vicker's hardness (Hv) of 250 and a temperature coefficient T.C.R (0° to 100° C.) of 7,850 ppm/°C. This wire material is wound 22 turns in a winding diameter of 1.0$\phi$. Each of the coils thus produced is held horizontally by a TO-5 type stem and is welded to give a coil length of 2.5 to 2.8 mm. After the coils were washed with an organic solvent such as an alcohol and then dried, the coils are used as the coils for the active portion S and the dummy portion D.

Next, powder of fine particles prepared in advance by uniformly dispersing $MnO_2$, and $Al_2O_3$ in a $Cu_2$-O-ZnO solid solution and an electro-deposition resin solution are mixed and stirred, and the resulting electro-deposition solution is transferred to an electro-deposition cup. Then, electro-deposition coating for both A.C. and D.C. is carried out on the upper surface of the coil so as to form a thick cylindrical film of $Cu_2O.ZnO.MnO_2.Al_2O_3$ on the upper surface.

After the film is sufficiently dried, a solution prepared by dissolving 1 g of $H_2PtCl_6.6H_2O$ in 10 cc of pure water is applied or dropped in such a manner that each application of 0.1 cc of this solution is dispersed throughout the thick film of the coil of the active portion. After drying, the coil is heated to a red heat state by an alcohol lamp having a wick so shaped as to be capable of heating only the thick film portion or by an infrared spot heater to decompose or burn out $H_2PtCl_6$ and the electrodeposition resin and to leave and deposit the Pt fine particles on the upper surface of the thick film. After this decomposition is completed, washing is carried out either with water or with vapor to completely remove the C( ions. After drying, the active portion is prepared On the other hand, a mixture of 1 part by weight of CuO, 2 parts by weight of $Cr_2O_3$, 1.5 parts by weight of $TiO_2$ and 1 part by weight of $Al_2O_3$ is added to 30 to 40 cc of an electro-deposition resin solution and is pulverized. The resulting electro-deposition solution is applied to the coil for the dummy portion, and the dummy portion is thus prepared.

The resistance value at 20° C. and the current value at the time of the application of D.C. 3 V are determined for each of the active portion and the dummy portion, and the resistance value at the time of the application of 3 V is determined by calculation. The sensor temperature is in advance obtained from $R_{3v}/R_{20}$, and the coils having substantially equal sensor temperature characteristics are selected as a pair. If such characteristics are the same, $V_o$ is almost constant even when the ambient temperature and the power source voltage change, and there can be obtained a stable sensor not causing the zero drift.

A cap is fitted to each coil, and after the measurement and inspection, an electric aging test is carried out for at least five days for the coil under the same condition as the condition of use of the coil. The caps of only the approved products are caulked to complete the sensor. The approved products have a sensitivity of 20 to 25 mV at a sensor temperature of 155° C.±3° C., a CO concentration of 500 ppm and a bridge voltage of 6 V, but have a sensitivity to $H_2$ of only 0 to 3 mV at a concentration of 500 ppm and a sensitivity to $C_2H_5OH$ of only 0 to 3 V at a concentration of 1,000 ppm.

EFFECTS OF THE INVENTION

As described above, the present invention uses the Fe.Pd system alloy wire material for the coil and selects the wire material having a specific diameter and satisfying the limited ranges of the specific resistance, the Vickers' hardness and the temperature coefficient. Furthermore, the present invention uses, as the catalyst for the active portion, the catalyst which is prepared by uniformly dispersing the Pt black in fine particles obtained by uniformly mixing $MnO_2$, $Al_2O_3$, etc, in the $Cu_2O$, ZnO solid solution. In this way, the present invention can remove gas sensitivities to other unnecessary gases such as $H_2$, $C_2H_5OH$, etc, and moreover can obtain the CO sensitivity even around 150° C. CuO and $Cr_2O_3$ are selected for the catalyst of the dummy portion so that the resistance characteristics of the active portion become substantially the same as those of the dummy portion, and porosity as well as adhesion are adjusted so that the relation $V_S = V_D$ can be always established. Accordingly, the zero drift does not occur despite changes in the ambient temperature and in the power source voltage, the change of the CO gas sensitivity can be prevented, and a measurement error can be avoided as much as possible.

Incidentally, the present invention aims at providing a sensor reliably detecting carbon monoxide at a concentration of 500 ppm with high sensitivity, but an environmental standard value of CO in every country in the worked requires a concentration of 50 ppm. However, there are scarcely any economical and convenient sensors which can make simple and continuous measurement. In other words, although the regulations are in effect, it is essentially necessary at present to use an electrolytic system sensor or a large scale sensor which is extremely troublesome to operate, such as a gas chromatograph, and all these sensors can hardly be suitable for practical, application. Further, if the thickness of the wire material is about 20 μm in the present invention, the coil resistance theoretically increases 2.25 times, so that even when $R_{20}$ is from 60 Ω to 120 Ω, a sensor for 12 V can be produced very easily by the coil having substantially the same number of turns. As a result, the CO gas sensitivity is 50 mV at 500 ppm or in other words, 50 mV at 50 ppm. Accordingly, the sensor according to the present invention has an extremely high possibility for the practical application, and studies are now being furthered.

I claim:

1. A contact combustion type carbon monoxide sensor characterized in that a coil of each of the active portion and a dummy portion is made of a Fe.Pd system alloy wire material having a thickness of 15 to 40 μm, a specific resistance $\rho_{20}$ of 35 to 46 μΩcm, a Vickers' hardness Hv of 200 to 300 and a temperature coefficient T.C.R of 7,000 to 8,500 ppm/°C. in the range of 0° C. to 100° C., a catalyst formed at the active portion comprises at least $Cu_2O$, ZnO, $MnO_2$ and Pt black, and a catalyst formed at the dummy portion comprises at least CuO and $Cr_2O_3$.

2. A contact combustion type carbon monoxide sensor according to claim 1, wherein a CO sensitivity at a bridge voltage of 6 to 12 V and a concentration of 500 ppm is 25 to 50 mV.

3. A contact combustion type carbon monoxide sensor according to claim 1, wherein said catalyst formed at each of the active portion and the dummy portion is formed cylindrically on the surface of each coil.

4. A contact combustion type carbon monoxide sensor according to claim 1, wherein a sensor temperature is set to 155° C.±3° C.

* * * * *